United States Patent [19]

Fourie

[11] Patent Number: 4,495,956
[45] Date of Patent: Jan. 29, 1985

[54] DEVICE FOR CLEANING TEETH

[76] Inventor: Phillippus J. Fourie, 34 Park Plaza, 21 Gregory Ave., Melrose North, Johannesburg, South Africa, 2196

[21] Appl. No.: 426,131

[22] Filed: Sep. 28, 1982

[51] Int. Cl.$^3$ .............................................. A61C 15/00
[52] U.S. Cl. .................................................. 132/92 R
[58] Field of Search ...................................... 132/92, 91

[56] References Cited

U.S. PATENT DOCUMENTS

| | | | |
|---|---|---|---|
| 1,316,807 | 9/1919 | Ross | 132/92 R |
| 1,582,000 | 4/1926 | Gesell | 132/92 R |
| 1,952,358 | 3/1934 | Bohm | 132/92 R |
| 2,837,098 | 6/1958 | Sorboro | 132/92 R |
| 4,005,721 | 2/1977 | Yasumoto | 132/91 |

Primary Examiner—Gregory E. McNeill
Attorney, Agent, or Firm—Cushman, Darby & Cushman

[57] ABSTRACT

A device for cleaning teeth of the kind known as a dental floss holder comprising a housing adapted to house a quantity of dental floss, a locking member having at least one aperture therein and a formation adapted to support a span of the dental floss. The device has at least one aperture therein (but preferably two) such that the floss in an operative arrangement of the device passes through the aperture in the device, thereafter forms the span and then passes through the aperture in the device, the arrangement being such that the floss passing through the aperture in the device also passes through the aperture in the locking member when the latter is in an operative position.

11 Claims, 7 Drawing Figures

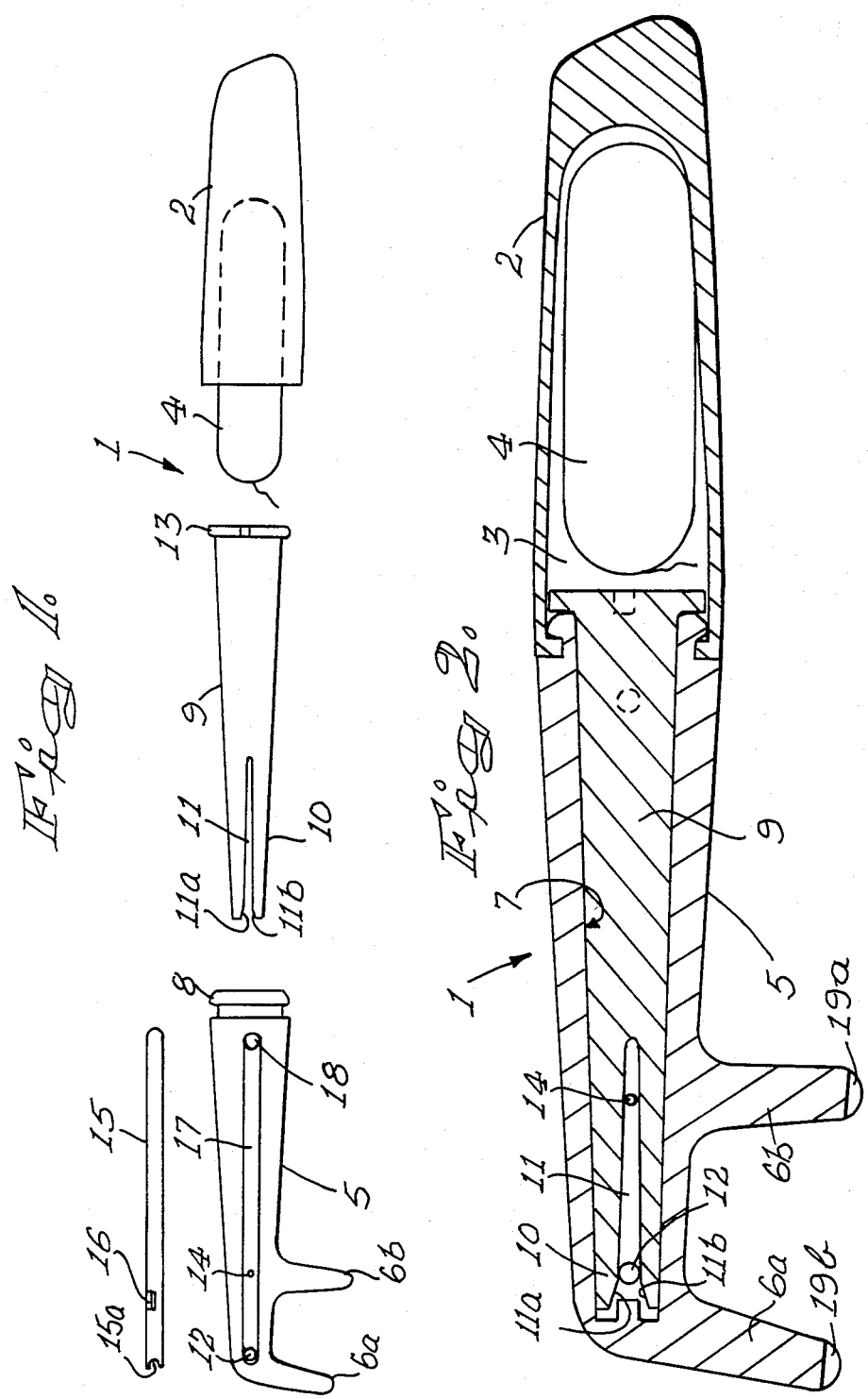

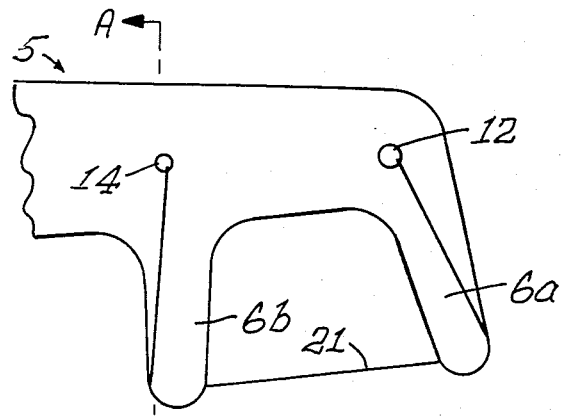
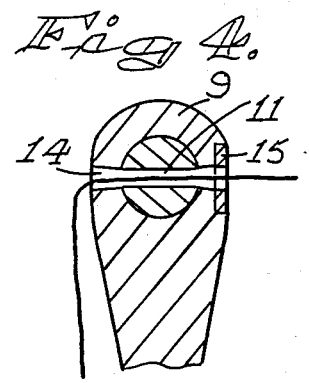
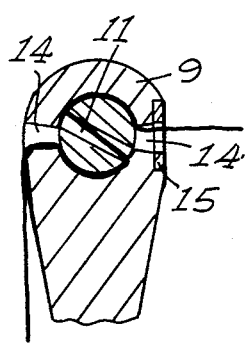
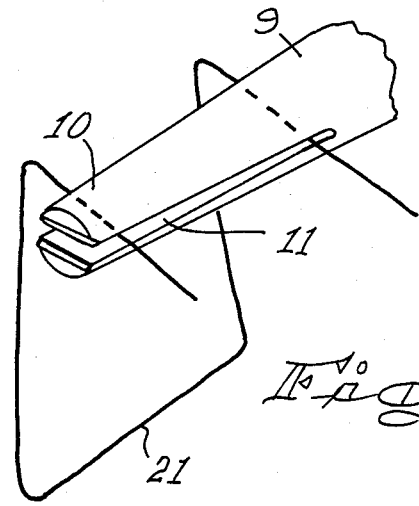
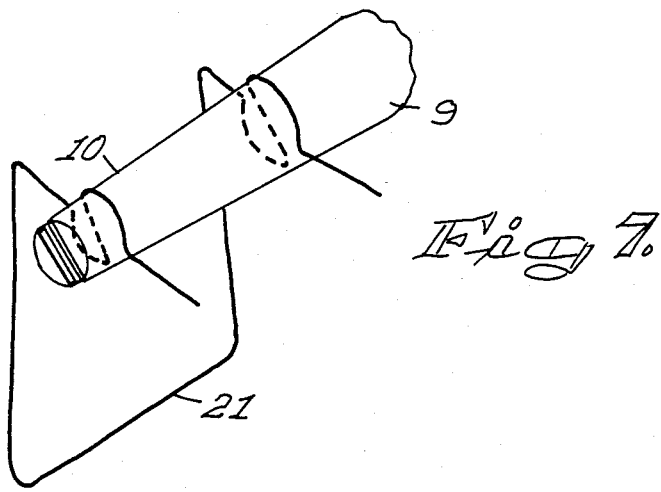

DEVICE FOR CLEANING TEETH

This invention relates to a device for cleaning teeth and more particularly to a device known in the art as a dental floss holder.

Dental floss holders are known which consist of two parts rotatable relative to one another about the longitudinal axis of the holder. A roll of dental floss is housed in one of the parts and the other part has a pair of arms across which the floss is led to form a span. The floss in such holders is passed through a hole extending through both parts so that upon rotation of the parts relative to one another the floss becomes wound onto one of the parts and thereby tautens the floss forming the span between the pair of arms.

Dental floss holders of the above kind may suffer from several disadvantages. For the holder to be effective in use it is essential that the floss be locked in the tautened position but locking may be insufficient with prior art holders. If the floss breaks, for instance in the region of the span between the two arms of the holder, it is necessary to re-thread the floss through the relevant holes in the holder. This may be difficult if not impossible with prior art holders. Such holders also generally have considerable lengths of floss exposed in the operative condition of the holders which is unsuitable as these lengths may become soiled and unsuitable for use when ultimately forming the span of floss across the arms of the holder.

It is accordingly an object of the invention at least to diminish one or more of the shortcomings outlined above.

A device for cleaning teeth according to the invention comprises a housing adapted to house a quantity of dental floss, a locking member having at least one aperture therein and a formation adapted to support a span of the dental floss, the device having at least one aperture therein such that the floss in an operative arrangement of the device passes through the aperture in the device, thereafter forms the span and thence passes through the aperture in the device, the arrangement being such that the floss passing through the aperture in the device also passes through the aperture in the locking member when the latter is in an operative position.

Further according to the invention the housing is defined by a housing member and the formation is a fork formation provided on a fork member, the housing member and the fork member being rotatable relative to one another about the longitudinal axis of the device.

Further according to the invention the locking member is a separate locking member receivable in a cavity in the fork member and is rotatable relative to the fork member co-axially therewith, the aperture in the device comprising a hole through the fork member, the aperture in the locking member comprising a slot therein located along its axis, the slot in an operative arrangement of the device being in register with the hole through the fork member.

Further according to the invention means are provided engaging the housing member and locking member so that rotation of the housing member relative to the fork member causes rotation of the locking member in the fork member.

Further according to the invention the hole in the fork member is one of a pair of holes, one hole being located in the region of the base of one arm of the fork formation, the other hole being located in the region of the base of the other arm of the fork formation, the arrangement being one wherein the floss passes, in an operative arrangement of the device, through one hole in the fork member and at the same time through the slot in the locking member, thereafter across the free ends of the fork formation to form the span of floss and thence through the other hole in the fork member and at the same time through the slot in the locking member.

Further according to the invention the locking member is of elongated configuration, the leading end of the locking member receivable in the cavity of the fork member having the slot formed therein in open ended fashion.

Further according to the invention the slot in the locking member decreases in width from the open end of the slot.

Further according to the invention the locking member is of circular cross-section and increases in cross-section from the leading end of the locking member.

Further according to the invention means are provided on the device for cutting the floss.

A preferred embodiment of the invention is described below by way of example with reference to the accompanying drawings in which:

FIG. 1 is an exploded view of a device according to the invention;

FIG. 2 is a cross-section of the device of FIG. 1 in assembled form on an enlarged scale;

FIG. 3 shows a part of the device of FIG. 2; and

FIGS. 4 to 7 illustrate the locking and tautening action of the device, FIGS. 4 and 5 being sections taken on line A—A of FIG. 3 and FIGS. 6 and 7 being perspective views of a part of the device.

The device 1 comprises a housing member 2 of generally cylindrical form defining a chamber 3 in its interior adapted to house a cocoon of dental floss 4.

A fork member 5 also of generally cylindrical form has a fork formation at one end thereof made up of two arms 6a, 6b and an annular shoulder 8 at its opposite end adapted to snap into engagement with the housing member 2. The fork member 5 has a cavity 7 along its axis adapted to receive an elongated locking member 9 which is rotatable relative to the fork member 5 co-axially therewith. The leading end 10 of the locking member 9 has a slot 11 therethrough extending along its axis. The slot is formed in open ended fashion and has diverging faces 11a, 11b at its end forming a mouth thereto. The slot 11 decreases in width from its open end. The locking member 9 is of circular cross section and increases in cross section from the leading end 10 thereof. At its other end the locking member 9 has a shoulder 13 which in the operative arrangement of the device engages the housing member 2 so that when the housing member is rotated about its axis relative to the fork member 5, the locking member 9 will rotate with the housing member 2. This may be achieved, for example, by providing a flat (not shown) on the shoulder 13 adapted to abut a complementary surface in the housing member 2.

At the base region of the arms 6a, 6b of the fork member 6 holes 12, 14 are formed through the fork member 5. The hole 12, that is the hole furthest from the housing member 2 is about twice the diameter of the hole 14. In the operative arrangement of the device, the slot 11 in the locking member 9 is in register with the holes 12, 14 in the fork member 5.

A metal strip 15 having a cutting edge 16 is provided to fit into a recess 17 formed in the fork member 5. A further hole 18 is provided through the wall of the fork member at the end of the recess 17 remote from the arms 6a, 6b. The metal strip 15 is suitably notched at 15a to ensure that the hole 12 is exposed when the strip is fitted in the recess 17.

In use, the cocoon of dental floss 4 is placed in the chamber 3 of the housing member 2 and the free end of the dental floss is passed from the interior of the fork member 5 through the hole 18. The free end of the dental floss is then passed through the hole 14 in the fork member from the side carrying the metal strip 15 and thereafter it is passed through notches 19a, 19b in the free ends of the arms 6a, 6b to form a span 21 of dental floss across the arms. The free end of the dental floss 4 is then passed through the hole 12 in the fork member 5 from the side opposite that carrying the metal strip 15 and is cut off on the cutting edge 16. Thereafter the locking member 9 is inserted into the fork member 5 so that the dental floss passing through the holes 12, 14 enters the slot 11. This is made easier by the flaring mouth of the slot 11 formed by the faces 11a, 11b.

In a preferred form, the metal strip 15 is fitted in the recess 17 in the fork member 5 after threading of the floss as described above so that the floss between the holes 18 and 14 is covered by the strip 15.

The use of a slot 11 in the locking member 9 greatly facilitates the threading of the dental floss as described above to render the device operative. The threading of the dental floss and its location in the slot 11 as described above are illustrated in FIGS. 4 and 6.

The fork member 5 and the housing member 2 are thereupon snapped together. If the housing member 2 is now rotated about its axis relative to the fork member 5, the dental floss 4 will be wound onto the locking member 9 as illustrated in FIGS. 5 and 7. This will serve to both lock and tauten the span 21 of dental floss extending across the arms 6a, 6b. The frictional force created by the floss being wound onto the locking member 9 causes the locking action.

It will be appreciated that the use of the two holes 12, 14 serve to lock the dental floss at each side of the span 21 which provides efficient locking necessary for satisfactory use of the device.

In this condition the device 1 is ready for use by a user to clean the regions between the user's adjoining teeth. After user of the housing member 2 may be rotated to its original position to release the locking action on the dental floss 4, a sufficient length of which may then be withdrawn from the device, cut off on the cutting edge 16 and discarded. Suitable stops may be provided to limit the extent to which the housing member 2 may be rotated relative to the fork members.

A difficulty encountered with dental floss holders is that if the floss breaks as a result or normal use, for instance at the span 21, the floss cannot be threaded through the relevant holes again. This difficulty is reduced in the holder described above in that the hole 12 is made sufficiently large to permit easy re-threading. For this reason the slot 11 is also wider near the open end thereof. To compensate for the loss of tensioning occasioned by the increased size of the hole 12 and slot 11, the locking member 9 is of larger diameter where it coincides with the hole 14 in the locking 14 so that more floss is here wound onto the locking member during the locking action.

As will be evident from FIG. 3, the dental floss is neatly located in the region of the arms 6a, 6b of the fork member where it is unlikely to become excessively soiled. Shallow recesses may be provided on the device to accommodate the dental floss where it appears on the exterior of the device to further diminish the chance of soiling.

Other embodiments of the invention may be made differing in matters of detail only from that described above and without departing from the scope of the invention described in the appended claims.

I claim:

1. A device for cleaning teeth comprising: a housing adapted to house a quantity of dental floss; a locking member having at least one aperture therein; and a formation adapted to support a span of the dental floss; said housing being defined by a housing member, and said formation comprising a fork formation provided on a fork member, and said housing member and fork member being rotatable relative to one another about the longitudinal axis of the device; said formation having at least one aperture therein such that floss from said housing, in an operative position, passes through said aperture and said formation, and thereafter forms the span of floss; and wherein in said operative position the floss from said housing also passes through said aperture in said locking member; and wherein said at least one aperture in said formation comprises at least one hole through the fork member, the aperture in the locking member comprising a slot therein located along its axis, the slot in said operative position being in registry with said at least one hole through said fork member.

2. A device according to claim 1 wherein said locking member is a separate locking member receivable in a cavity in said fork member, and rotatable relative to said fork member coaxially therewith.

3. A device according to claim 1 including means for cutting the floss operatively mounted on said formation.

4. A device as recited in claim 1 wherein said locking member is mounted in association with said formation for relative rotational movement with respect thereto.

5. A device according to claim 2 in which means are provided engaging the housing member and locking member so that rotation of the housing member relative to the fork member causes rotation of the locking member in the fork member.

6. A device as recited in claim 3 wherein said locking member is mounted in association with said formation for relative rotational movement with respect thereto.

7. A device according to claim 3 in which said at least one hole in the fork member comprises a pair of holes, a first hole being located in the region of the base of one arm of the fork formation, a second hole being located in the region of the base of the other arm of the fork formation, the arrangement being one wherein the floss passes, in said operative position, through said first hole in the fork member and at the same time through the slot in the locking member, across the free ends of the fork formation to form the span of floss, and through said second hole in the fork member and at the same time through the slot in the locking member.

8. A device according to claim 2 in which the locking member is of elongated configuration, the leading end of the locking member received in the cavity of the fork member with the slot formed in said leading end so that said locking member has an open-ended slot located in said cavity.

9. A device according to claim 7 wherein said locking member is of elongated configuration, the leading end of said locking member received in said cavity of said fork member, with said slot formed in said leading end so that said locking member has an open end located in said cavity.

10. A device according to claim 8 in which the slot in the locking member decreases in width from the open end of the slot.

11. A device according to claim 8–10 in which the locking member is of circular cross-section and increases in cross-section from the leading end of the locking member.

* * * * *